(12) United States Patent
Honda et al.

(10) Patent No.: US 6,679,854 B2
(45) Date of Patent: Jan. 20, 2004

(54) POSTPARTUM SUPPORTING APPARATUS

(75) Inventors: Yuka Honda, Tokyo (JP); Hirokazu Ono, Kawasaki (JP); Kentaro Kimura, Saitama (JP)

(73) Assignee: Tanita Corporation, Tokyo (JP)

( * ) Notice: Subject to any disclaimer, the term of this patent is extended or adjusted under 35 U.S.C. 154(b) by 48 days.

(21) Appl. No.: 10/012,451

(22) Filed: Dec. 12, 2001

(65) Prior Publication Data

US 2002/0087102 A1 Jul. 4, 2002

(30) Foreign Application Priority Data

Dec. 28, 2000 (JP) ........................................ 2000-400793

(51) Int. Cl.[7] ............................ A61B 5/103; A61B 5/117
(52) U.S. Cl. ..................................................... 600/587
(58) Field of Search ................................. 600/587, 547, 600/551, 591

(56) References Cited

U.S. PATENT DOCUMENTS

| 4,773,492 A |   | 9/1988 | Ruzumna |   |
|---|---|---|---|---|
| 6,402,699 B1 | * | 6/2002 | Kodama et al. | 600/551 |
| 6,434,422 B1 | * | 8/2002 | Tomoda et al. | 600/547 |

FOREIGN PATENT DOCUMENTS

JP 2001-70274 3/2001

* cited by examiner

Primary Examiner—Brian Szmal
(74) Attorney, Agent, or Firm—McDermott, Will & Emery (57) ABSTRACT

Disclosed is a postpartum supporting apparatus, comprising a storage unit and an output unit. The storage unit stores reference data that is used to compare with postpartum measurement data representing an index of body condition after childbirth for determining whether the progress of restoration of the body condition after childbirth is good or not. The output unit outputs said reference data in order to compare with the postpartum measurement data representing the index of body condition after childbirth.

61 Claims, 9 Drawing Sheets

FIG. 3(a)
Body Weight Increase During Pregnancy: less than 8kg
Mother's Milk or Combination of Mother's Milk and Bottle Milk

FIG. 3(b)
Body Weight Increase During Pregnancy: less than 8kg
Bottle Milk

FIG. 3(c)

Body Weight Increase During Pregnancy: not less than 8kg
Mother's Milk or Combination of Mother's Milk and Bottle Milk

FIG. 3(d)

Body Weight Increase During Pregnancy: not less than 8kg
Bottle Milk

FIG. 4

| Result of Comparison | Advice Information |
|---|---|
| Measured Value > Upper Limit | Take care of not eat too much. |
| Upper Limit ≧ Measured Value ≧ Lower Limit | Good! Keep this condition. |
| Lower Limit > Measured Value | Intake sufficient nutrition and pay attention not to excessively reduce the weight. |

Enter date and time

AUG./12/2000
15:35 P.M.

FIG. 7

| Enter following data | |
|---|---|
| Age | 23 |
| Height | 163.5cm |
| Body Weight Before Pregnancy | 50kg |
| Body Weight Immediately Before Childbirth | 60kg |
| Body Fat Rate One Month After Childbirth | 27.4% |
| Expected Date of Childbirth | FEB./15/'00 |
| Date of Childbirth | FEB./13/'00 |
| 1.Mother's Milk or Combination of Mother's Milk and Bottle Milk : 2.Bottle Milk | 1 |

POSTPARTUM SUPPORTING APPARATUS

BACKGROUND OF THE INVENTION

1. Field of the Invention

The present invention relates to a postpartum supporting apparatus for supporting a woman for successful restoration of body condition after childbirth. The words "body condition", as used herein, means body weight condition, body fat condition, and the like.

2. Prior Art

In general, the body condition for a woman significantly changes throughout the period of pregnancy from its initial stage to the final stage or childbirth, and thereafter, the woman gradually restores to the original body condition as was before the pregnancy. If restoration of the body condition after childbirth is not good it means that the health of the woman is adversely affected. For example, it may happen that the woman develops gestosis or have difficult delivery at the time of next pregnancy. Otherwise, the woman may suffer from any abnormal of fecundity, any malfunction of ovulation and any adult disease. Therefore, there is a need for precisely determining whether the progress of restoration of the body condition after childbirth is good or not and, if not, rapidly providing certain treatments accordingly.

A patent application has been filed, entitled "Method and Apparatus for Judging Recovery of Physical Condition in Puerperium" (see TOKUGANHEI No. 11-250650). According to this patent application the physical condition is taken as the body condition and bioelectrical impedance characteristic is used as an index of the physical condition. Then, an evaluation about the restoration of physical condition after childbirth is performed depending upon change in bioelectrical impedance characteristics as measured after childbirth, or upon the result of comparison of bioelectrical impedance characteristics as measured before pregnancy or at the initial stage of pregnancy and after childbirth.

However, if the change in bioelectrical impedance characteristics is used for the evaluation, it can be determined that the physical condition tends to be restored, but it is not sure that the progress of restoration of physical condition is good or not. On the other hand, if the result of comparison of bioelectrical impedance characteristics as measured before pregnancy or at the initial stage of pregnancy and after childbirth is used for the evaluation, how about the progress of restoration of physical condition relative to that before pregnancy or at the initial stage of pregnancy can be known, but it is also not sure that the progress of restoration of physical condition is good or not.

In view of the above, the present invention aims at reliably making decision of whether the progress of restoration of the body condition after childbirth is good or not. This is achieved, according to the present invention, by providing a postpartum supporting apparatus for outputting reference data that is used to compare with postpartum measurement data representing an index of body condition after childbirth for determining whether the progress of restoration of the body condition after childbirth is good or not; and by providing a postpartum supporting apparatus for comparing such measurement data with the reference data and for outputting the result of the comparison.

SUMMARY OF THE INVENTION

According to one aspect of the present invention there is provided a postpartum supporting apparatus, comprising a storage unit and an output unit, whereby, the storage unit stores reference data that is used to compare with postpartum measurement data representing an index of body condition after childbirth for determining whether the progress of restoration of the body condition after childbirth is good or not, and said output unit outputs said reference data in order to compare with the postpartum measurement data representing the index of body condition after childbirth. The apparatus further comprises a measurement data input unit. The measurement data input unit inputs the postpartum measurement data representing the index of body condition after childbirth, and said output unit further outputs such postpartum measurement data. The reference data is formed for each of factors affecting the restoration of body condition. The apparatus further comprises a factor data input unit and a selection unit. The factor data input unit inputs the factor data for a user and the selection unit selects any one of the reference data based on the input factor data. The output unit outputs the selected reference data.

According to another aspect of the present invention there is provided a postpartum supporting apparatus, comprising: a measurement data input unit; a storage unit; a comparator unit; and an output unit, whereby, the measurement data input unit inputs postpartum measurement data representing an index of body condition after childbirth, the storage unit stores reference data that is used to compare with the measurement data for determining whether the progress of restoration of the body condition after childbirth is good or not, the comparator unit compares the measurement data with the reference data, and the output unit outputs the result of said comparison. The result of comparison may be the difference between the measurement data and the reference data. The storage unit further stores advice information useful for guiding the restoration of body condition after childbirth according to the result of the comparison; the comparator unit further selects the advice information based on the result of the comparison; and the output unit outputs at least the selected advice information. The reference data is formed for each of factors affecting the restoration of body condition. The apparatus further comprises a factor data input unit and a selection unit. The factor data input unit inputs the factor data for a user and the selection unit selects any one of the reference data based on the input factor data. The comparator unit compares the selected reference data with the measurement data.

The measurement data input unit may be at least either one of a measurement unit for measuring the index of the body condition and a user input unit for inputting by a user. The factor data input unit may be at least either one of a measurement unit for measuring the factor data and a user input unit for inputting by a user. The body condition may be body weight condition or body fat condition. The factor affecting the body condition may be at least either one of a body weight increase during the period of pregnancy, a manner of lactation and an age of a user. The reference data may be defined as the value representing good body condition at some points in time after childbirth.

BRIEF DESCRIPTION OF THE DRAWINGS

Now, the present invention will be described in more detail with reference to the accompanying drawings, in which.

DESCRIPTION OF THE PREFERRED EMBODIMENTS

A postpartum supporting apparatus according to the present invention uses body weight condition and body fat condition as the body condition for determining whether the progress of restoration after childbirth is good or not. In particular a body weight and a body weight increase relative to that before pregnancy are used as an index of the body weight condition. In addition, a body fat rate calculated based on the bioelectrical impedance is used as an index of the body fat condition. In this regard, the body fat condition especially more than one month after childbirth is used for determining whether the progress of restoration is good or not. The reason for which is that during the period from the initial stage of pregnancy up to one month after childbirth an amount of water in the body of a user significantly fluctuates to greatly affect the bioelectrical impedance, and therefore, the reliability of the body fat rate calculated based on such bioelectrical impedance becomes lower.

Figure 1:
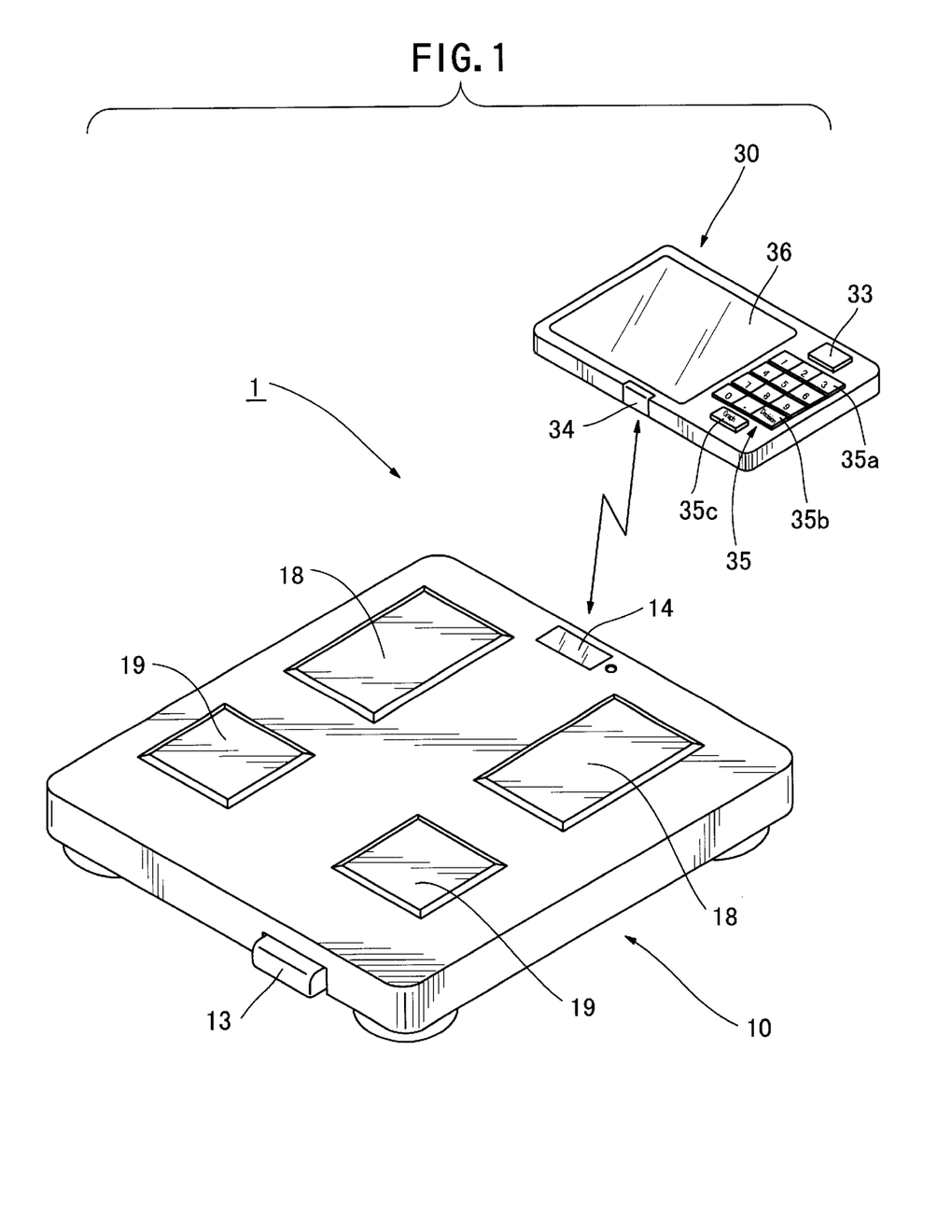
FIG. 1 is a perspective view of a postpartum supporting apparatus according to one embodiment of the present invention.
Figure 2:
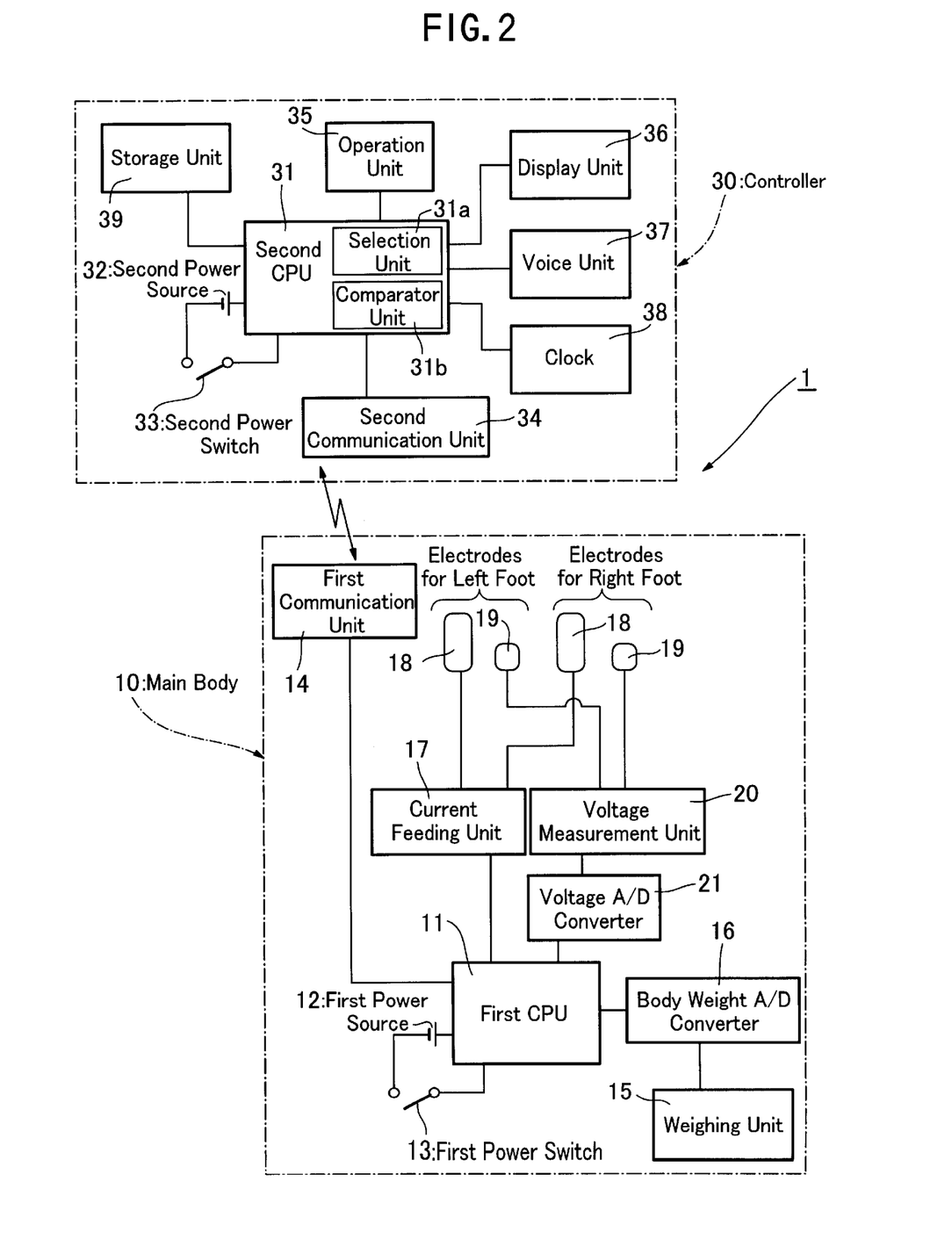
FIG. 2 is a block diagram of the apparatus in FIG. 1.

Referring to the drawings, FIG. 1 is a perspective view of a postpartum supporting apparatus according to one embodiment of the present invention, and FIG. 2 is a block diagram of the apparatus in FIG. 1. The apparatus 1 comprises a main body 10 and a controller 30 both of which are communicated to each other using an infrared ray. The main body 10 includes a first CPU 11; a first power source 12; a first power switch 13; a first communication unit 14; a weighing unit 15; a body weight A/D converter 16; a current feeding unit 17; a pair of current feeding electrodes 18; a pair of voltage measurement electrodes 19; a voltage measurement unit 20; and a voltage A/D converter 21. On the other hand, the controller 30 includes a second CPU 31; a second power source 32; a second power switch 33; a second communication unit 34; an operation unit 35; a display unit 36; a voice unit 37; a clock 38; and a storage unit 39.

The first CPU 11 performs an arithmetic operation and controls the operation of the whole main body 10. The first power source 12 feeds an electric power to the main body 10 according to the position of the first power switch 13. The first communication unit 14 sends and receives measurement data, measuring commands, etc. to and from the second communication unit 34 via the infrared ray communication. The weighing unit 15 measures the body weight of a user and outputs an analog signal representing the body weight. The body weight A/D converter 16 converts the analog signal into a digital signal. The first CPU 11 calculates the body weight based on this digital signal. The current feeding unit 17 feeds an electric current for measurement, which electric current is fed to the user via a pair of current feeding electrodes 18 on which tiptoes of both feet of the user are positioned. The voltage measurement unit 20 detects a voltage between any two points of the user via a pair of voltage measurement electrodes 19 on which heels of both feet of the user are positioned, and outputs an analog signal representing the voltage. The voltage A/D converter 21 converts the analog signal into a digital signal. The first CPU 11 calculates the body fat rate based on the digital signal.

The second CPU 31 performs an arithmetic operation and controls an operation of the whole controller 30, and it includes a selection unit 31a and a comparator unit 31b. The second power source 32 feeds an electric power to the controller 30 according to the position of the second power switch 33. The second communication unit 34 sends and receives the measurement data to and from the first communication unit 14 via the infrared ray communication, as described before. The operation unit 35 includes a ten-key 35a, a decision key 35b and a graph key 35c that are depressed by a user for operation of the apparatus 1 and entering of the personal information. The display unit 36 displays the measurement results and the guide information for operation of the apparatus. The voice unit 37 announces the end of the measurement. The clock 38 provides date information for the measurement.

The storage unit 39 stores the entered personal information and the measured body weight and body fat rate together with the date information. In addition, stored in the storage unit 39 in advance as the reference data are: a reference body weight increase that is used to compare with a body weight increase measured after childbirth for determining whether the progress of restoration for the weight condition after childbirth is good or not; and a reference body fat rate that is used to compare with a body fat rate measured more than one month after childbirth for determining whether the progress of restoration for the body fat condition is good or not.

FIGS. 3(a), 3(b), 3(c) and 3(d) show an example of a reference data or a reference body weight increase. For each of factors affecting the restoration for the body weight condition after childbirth, the reference body weight increase consists of: an ideal body weight increase at some points in time after childbirth (or an ideal reference body weight increase), as indicated by ①; an upper limit for suitable body weight increase at some points in time after childbirth (or an upper limit reference body weight increase), as indicated by ②; and a lower limit therefor (or a lower limit reference body weight increase), as indicated by ③. The factors affecting the restoration for the body weight condition after childbirth are: a body weight increase during the period of pregnancy (not less than or less than 8 kg); and a manner of lactation (only mother's milk or combination of mother's milk and bottle milk, or only bottle milk). The body weight increase during the period of pregnancy affects the restoration of the body weight condition. For example, assuming that the energy consumption is kept constant, if the body weight increase during the period of pregnancy is greater, it takes longer time to restore to the original body weight as was before the pregnancy. In addition, the manner of lactation also affects the restoration of the body weight condition. In particular it is generally known that a fat of 5.5 kg at average is accumulated within the body to allow for mother's milk given to a newborn baby. Therefore, if the amount of mother's milk given to a newborn baby is smaller, the fat accumulated within the body will not be consumed, and therefore, it takes longer time to restore to the original body weight as was before the pregnancy.

The ideal reference body weight increase as indicated by ① has been derived in such manner that the body weight increase for each of a plurality of women who have given birth is measured at the predetermined intervals starting after childbirth, the women are divided into groups according to the factors as above, an average for the body weight increase as measured at such predetermined intervals is calculated for the women belonging to the same group, and the approximated curves are plotted for each of the groups. The upper limit ②and the lower limit ③for body weight increase have been derived in such manner that the standard deviation calculated with the average is added to or subtracted from the average to produce values from which the approximated curves are plotted.

Figure 3A:
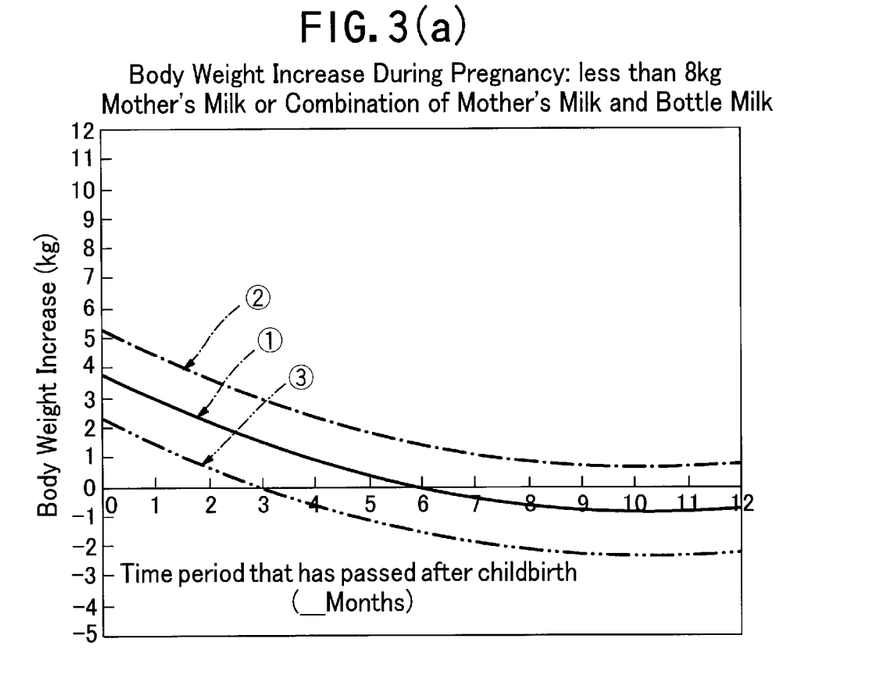
FIGS. 3(a), 3(b), 3(c), and 3(d) show an example of reference body weight increase for different factors.
Figure 3B:
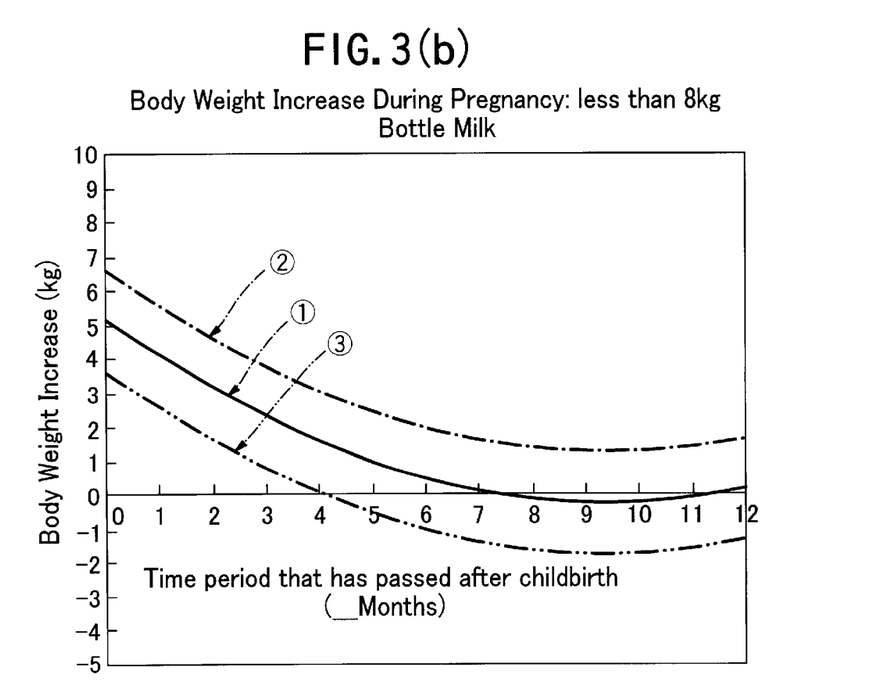
Figure 3C:
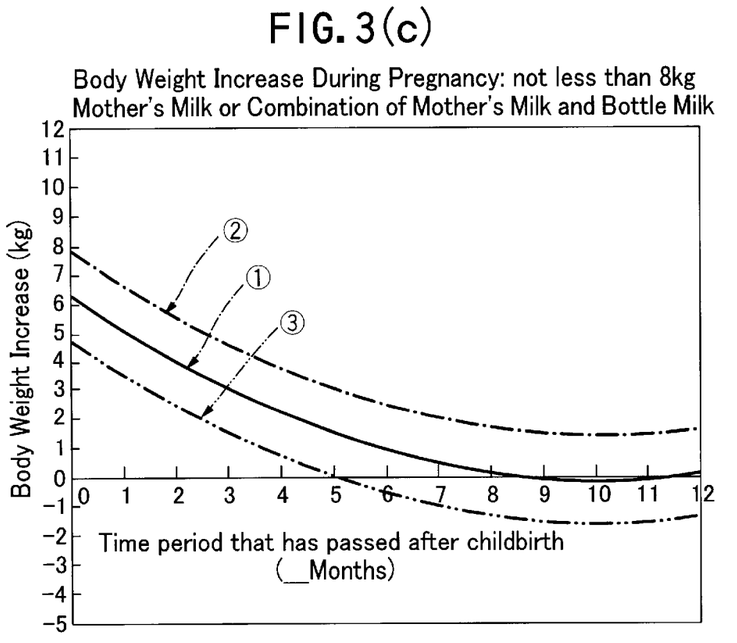
Figure 3D:
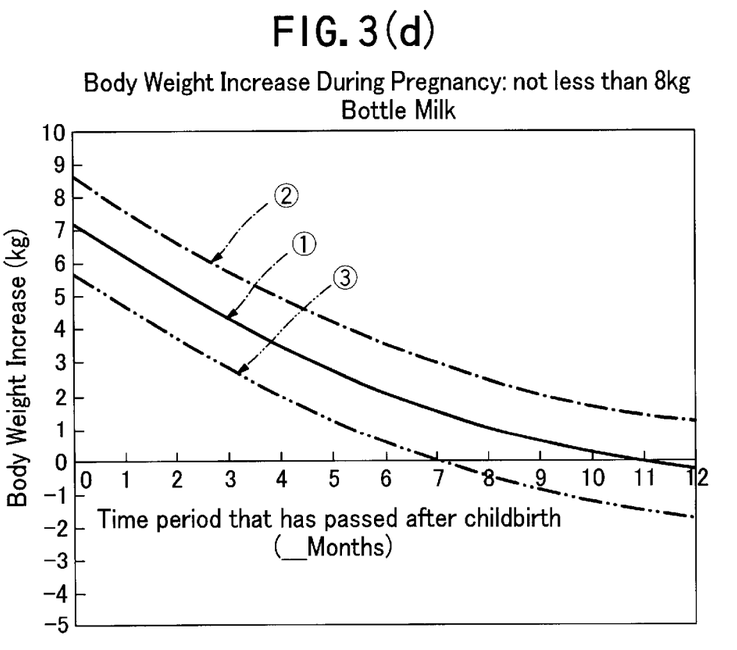

In particular, FIG. 3(a) shows the reference data or reference body weight increase in case where the body weight increase during the period of pregnancy is less than 8 kg and the manner of lactation is only mother's milk or combination of mother's milk and bottle milk. In this case the graph shows such tendency that it takes minimum time period to restore to the original body weight before pregnancy. FIG. 3(b) shows the reference data or reference body weight increase in case where the body weight increase during the period of pregnancy is less than 8 kg and the manner of lactation is only bottle milk. The graph in FIG. 3(b) shows such tendency that it takes more time period to restore to the original body weight before pregnancy than the case of FIG. 3(a) because of only bottle milk used for lactation. FIG. 3(c) shows the reference data or reference body weight increase in case where the body weight increase during the period of pregnancy is not less than 8 kg and the manner of lactation is only mother's milk or combination of mother's milk and bottle milk. In this case the graph shows such tendency that it takes more time period to restore to the original body weight before pregnancy than the case of FIG. 3(a) because of larger increase in body weight during the period of pregnancy. FIG. 3(d) shows the reference data or reference body weight increase in case where the body weight increase during the period of pregnancy is not less than 8 kg and the manner of lactation is only bottle milk. In this case the graph shows such tendency that it takes maximum time period to restore to the original body weight before pregnancy.

On the other hand, another reference data or reference body fat rate consists of: an ideal body fat rate at more than one month after childbirth (or an ideal reference body fat rate); an upper limit for suitable body fat rate at more than one month after childbirth (or an upper limit reference body fat rate); and a lower limit therefor (or a lower limit reference body fat rate), for each of factors affecting the restoration for the body fat condition after childbirth. In particular the factors are: a body fat rate at one month after childbirth; and a manner of lactation. The reference body fat rate has been derived from the measurement data of body fat rate for several women who have given birth, as in the case of the reference body weight increase.

Figure 4:
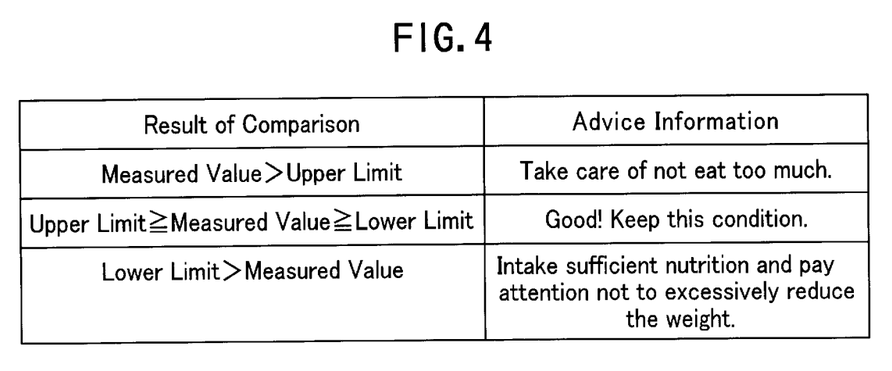
FIG. 4 shows the result of comparison of the measurement and the reference values and the corresponding advice information.

The storage unit 39 stores advice information useful for guiding the restoration of body weight and body fat condition after childbirth, in advance. The advice information is stored for each of the results of comparison between the measurement data and the reference data. FIG. 4 shows advice information for the body weight condition, by way of example. The advice information for body weight condition is defined for each of those cases where the measured body weight increase exists in the range between upper and lower limits for reference body weight increase and the progress of restoration of body weight condition is determined good; where the measured body weight increase exceeds the upper limit for reference body weight increase and the progress of restoration of body weight condition is determined not good; and where the measured body weight increase falls under the lower limit for reference body weight increase and the progress of restoration of body weight condition is determined not good. In similar manner, the advice information for body fat condition is defined for each of the cases where the measured body fat rate exists in the range between upper and lower limits for reference body fat rate; where it exceeds the upper limit for reference body fat rate; and where it falls under the lower limit for reference body fat rate.

The selection unit 31a in the second CPU 31 selects the reference body weight increase for a user according to the body weight increase during the period of pregnancy and the manner of lactation for the user. It also selects the reference body fat rate for the user according to the body fat rate measured one month after childbirth and the manner of lactation for the user.

The comparator unit 31b compares the measured body weight increase with the upper and lower limits for reference body weight increase, and selects the advice information according to the result of comparison. It also derives the difference between the measured body weight increase and the ideal reference body weight increase. The comparator unit 31b further compares the body fat rate measured more than one month after childbirth with the upper and lower limits for reference body fat rate, and selects the advice information according to the result of comparison. It also derives the difference between the body fat rate measured more than one month after childbirth and the ideal reference body fat rate.

Figure 5:
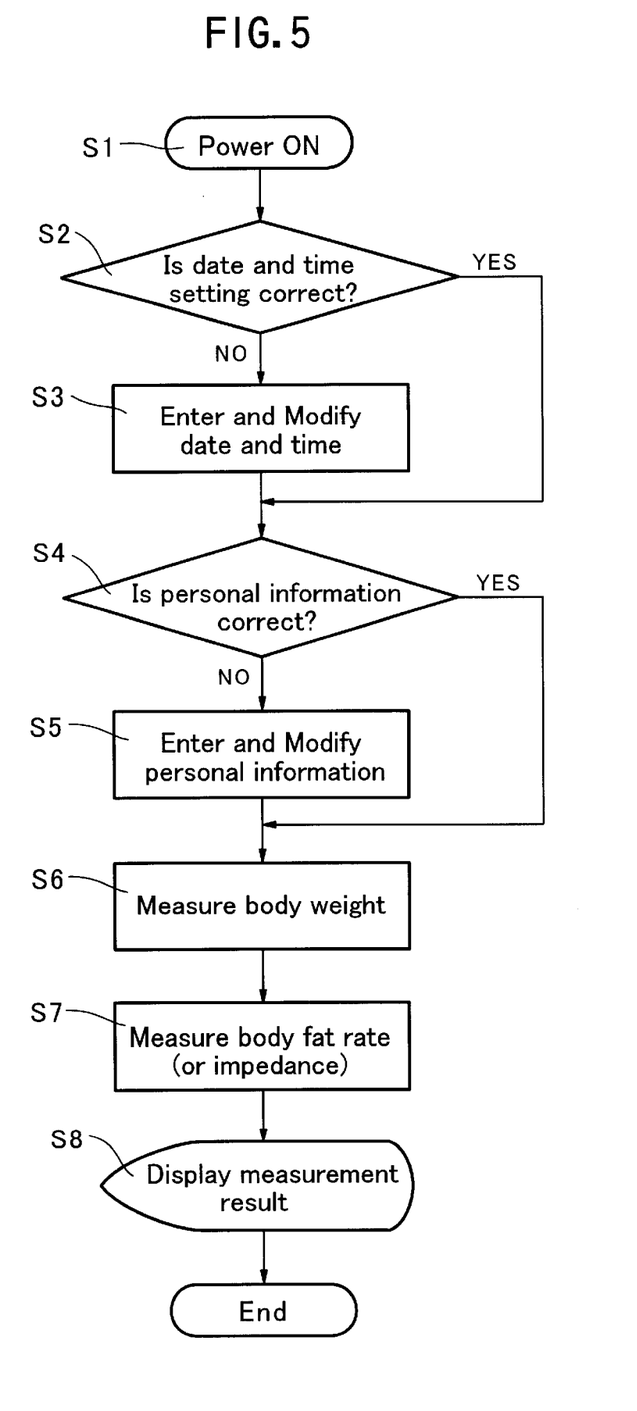
FIG. 5 is a flow chart illustrating an operation of the postpartum supporting apparatus in FIG. 1.
Figure 6:
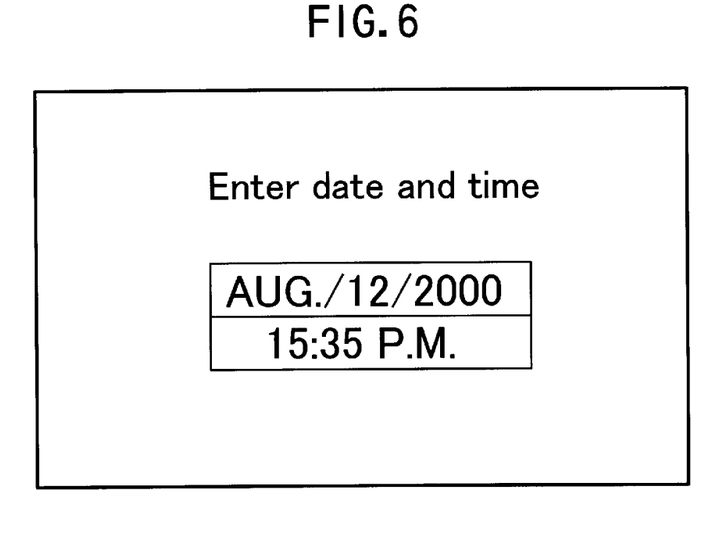
FIG. 6 shows an example of a date and time screen.

FIG. 5 is a flow chart illustrating an operation of a postpartum supporting apparatus in FIG. 1. Referring to FIG. 5, in step S1, the user turns ON the first and second power switches 13 and 33. Then, in step S2, the date screen is displayed on the display unit 36. As shown in FIG. 6, the current date and the time of a day produced by the clock 38 are displayed on the date screen. The user, then, decides as to whether the current date and the time displayed on the screen are correct or not. If they are correct (or Yes in step S2), the user depresses the decision key 35b to proceed to the step S4. But, if they are not correct (or No in step S2), the user enters the correct date and the time using the ten-key 35a with the aid of the guidance of a cursor on the display unit 36, and then, depresses the decision key 35b. In response thereto, the time setting of the clock 38 is modified to correspond to the date and time entered.

Figure 7:
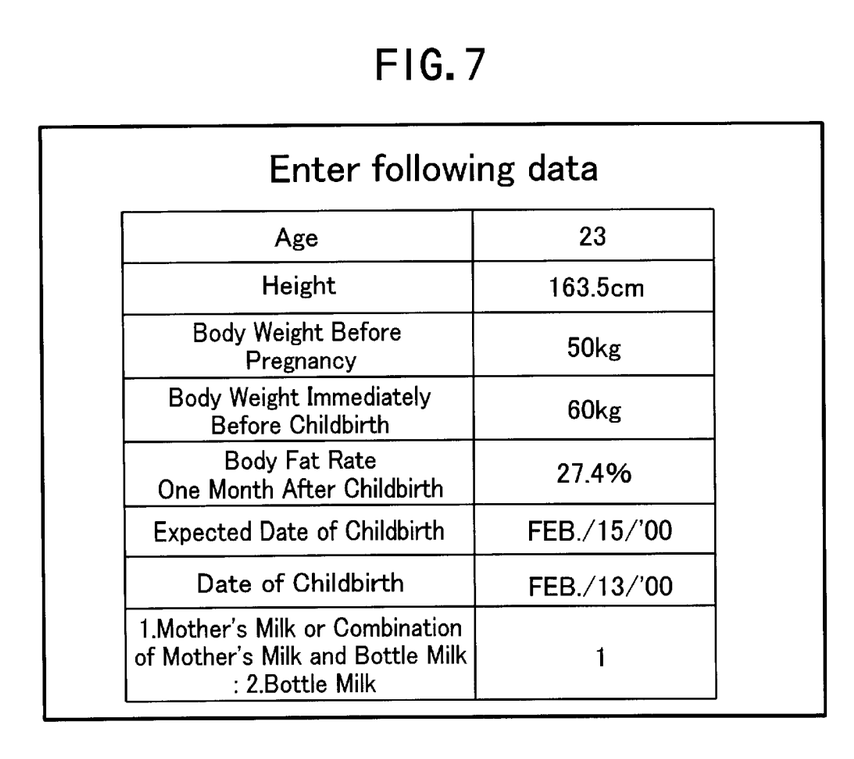
FIG. 7 shows an example of a personal information screen.

Then, in step S4, a personal information screen is displayed on the display unit 36. As shown in FIG. 7, the personal information stored in the storage unit 39 is displayed on the personal information screen. The personal information includes the age, height, body weight before pregnancy, body weight immediately before childbirth, body fat rate one month after childbirth, the expected date of childbirth, the date of childbirth, and manner of lactation (only mother's milk or combination of mother's milk and bottle milk, or only bottle milk). The user, then, determines as to whether the personal information displayed is correct or not. If they are correct (or Yes in step S4), the user depresses the decision key 35b to proceed to step S6. But, if they are not correct (or No in step S4), the user enters the correct personal information using the ten-key 35a with the aid of guidance of the cursor on the display unit 36 in step S5, and depresses the decision key 35b. In response thereto, the personal information stored in the storage unit 39 is replaced with the entered personal information.

In step S6 a message "Mount on the apparatus with tiptoes and heels of your feet contact with electrodes" is displayed on the display unit 36, and a measurement command is sent from the second communication unit 34 to the first communication unit 14. The user, then, mounts on the main body 10 with tiptoes of both feet contact with a pair of current feeding electrodes 18 and heels of both feet contact with a pair of voltage measurement electrodes 19. Thereafter, the body weight of the user is measured in the previous manner through the weighing unit 15, the body weight A/D converter 16 and the first CPU 11.

In step S7 the body fat rate of the user is measured in the previous manner through the current feeding unit 17, a pair of current feeding electrodes 18, a pair of voltage measurement electrodes 19, the voltage measurement unit 20, the voltage A/D converter 21 and the first CPU 11. The measured body weight and the body fat rate are sent from the first communication unit 14 to the second communication unit 34, and then, stored the storage unit 39 together with the data information from the clock 38.

In step S8 the difference between the body weight immediately before childbirth and the body weight before pregnancy as entered in step S5, namely the body weight increase during the period of pregnancy is calculated by the second CPU 31. Depending on this body weight increase during the period of pregnancy and the manner of lactation as entered in step S5, the selection unit 31a functions to select the user specific reference body weight increase among those stored in advance in the storage unit 39 (see FIGS. 3(a) to (d)). For a user having the profile as shown in FIG. 7, for example, the body weight increase during the period of pregnancy is 10 kg and the manner of lactation is only mother's milk or combination of mother's milk and bottle milk. Therefore, the selection unit selects the reference body weight increase as shown in FIG. 3(c) as the reference data. Then, the comparator unit 31b derives the difference between the body weight measured now and the body weight before pregnancy as entered in step S5, namely the body weight increase measured now. In addition, the time period that has passed since the date of childbirth up to now is calculated from the date on which the measurement is performed now and the date of childbirth as entered in step S5. Then, the reference body weight increase corresponding to such time period is selected as the reference for comparison among the reference body weight increase as selected by the selection unit 31a. Next, comparison is made between the body weight increase measured now and the upper and lower limits for reference body weight increase selected as the reference for comparison, and the advice information corresponding to the result of comparison is selected among those advice information for body weight condition stored in the storage unit 39 in advance (see FIG. 4). In addition, the difference between the body weight increase measured now and the ideal reference body weight increase selected as the reference for comparison is calculated.

If the date on which the measurement is performed now is more than one month after childbirth, the selection unit 31a selects the user specific reference body fat rate among those reference body fat rate stored in the storage unit 39, based on the body fat rate one month after the childbirth and the manner of lactation as entered in step S5. Then, the comparator unit 31b selects the reference body fat rate corresponding to the time period that has passed since the date of childbirth up to now as the reference for comparison among those reference body fat rate selected by the selection unit 31a. Next, comparison is made between the body fat rate measured now and the upper and lower limits for reference body fat rate selected as the reference for comparison, and the advice information corresponding to the result of comparison is selected among those advice information for body fat condition stored in the storage unit 39 in advance. In addition, the difference between the body fat rate measured now and the ideal reference body fat rate selected as the reference for comparison is calculated.

Figure 8:
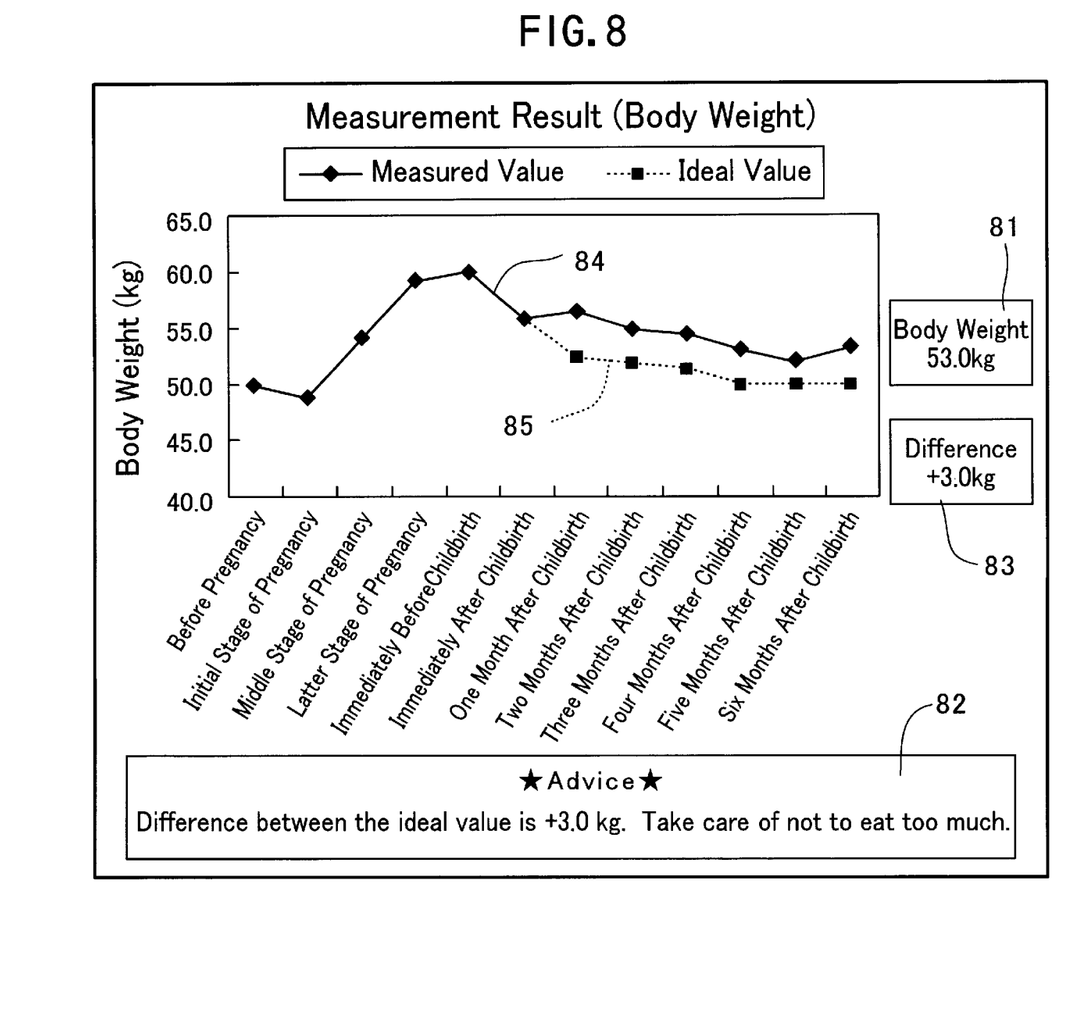
FIG. 8 shows an example of a body weight measurement result screen.

Then, a body weight measurement result screen is displayed on the display unit 36. As is apparent from FIG. 8, the body weight measurement result screen includes the body weight 81 measured now; the advice information 82 provided by the comparator unit 31b; the difference 83 between the body weight increase measured now and the ideal reference body weight increase; a curve 84 showing the body weight measured at the predetermined interval starting before pregnancy up to now; and a curve 85 showing the ideal reference body weight during the period from the date of childbirth up to now. The ideal reference body weight of the user is calculated by adding the ideal reference body weight increase selected by the selection unit 31a to the body weight before pregnancy as entered in step S5. The curves 84 and 85 may represent the body weight increase. However, the body weight is considered more preferable for the user than the body weight increase that must be derived by an additional calculation after measurement of the body weight. Therefore, it is preferable to display the body weight.

Figure 9:
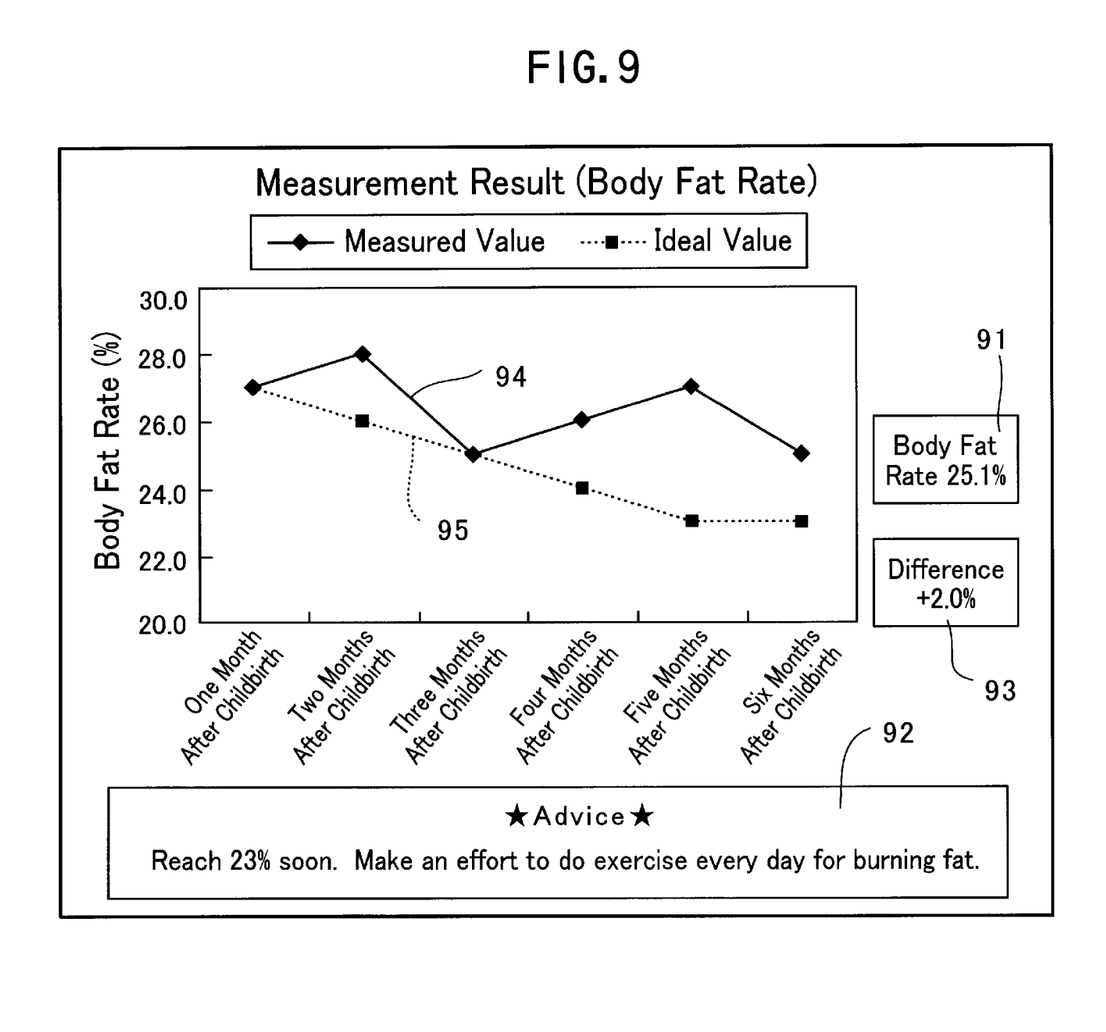
FIG. 9 shows an example of a body fat rate measurement result screen.

If the date on which the measurement is made now is more than one month after the date of childbirth, the graph key 35c is depressed to display a body fat rate measurement result screen on the display unit 36, instead of the body weight measurement result screen. As shown in FIG. 9, the body fat rate measurement result screen also includes the body fat rate 91 measured now; the advice information 92 provided by the comparator unit 31b; the difference 93 between the body fat rate measured now and the reference body fat rate; a curve 94 showing the body fat rate measured at the predetermined interval starting from one month after childbirth up to now; and a curve 95 showing the ideal reference body fat rate during the period from one month after childbirth up to now.

In the embodiment as described above, the body condition for which the restoration after childbirth is determined good or not was the body weight and the body fat rate. However, the present invention is not limited to such body condition, but other body condition such as the waist size may be used.

The factors affecting the restoration of body weight and body fat condition after childbirth may include an age of a user, a ratio of body weight increase during pregnancy to body weight before pregnancy, and the like, in addition to body weight increase during pregnancy and manner of lactation. Therefore, the reference body weight increase and the reference body fat rate may be produced according to the age of users and the ratio of body weight increase during pregnancy to body weight before pregnancy.

In the embodiment as described above, the measurement data such as body weight increase and body fat rate were entered via measurement by the weighing unit and the like. Alternatively user may enter such measurement data with the ten-key and the like. In such case the postpartum supporting apparatus may be configured in significantly simple manner without any measuring unit.

Furthermore, in the embodiment as described above, some of the personal information, such as the body weight before pregnancy, the body weight immediately before childbirth, and the body fat rate one month after childbirth were entered by the user using the ten-key. Such personal information may be got and entered with the weighing unit and other measuring device.

In addition to the measurement result, the reference body weight increase and the reference body fat rate in future may be displayed as the target values. Alternatively, only the reference body weight increase and the reference body fat rate in future may be displayed as the target values without the measurement result.

The measurement result may be output through the voice unit or the printer, in addition to be displayed on the display unit.

It is apparent from the foregoing that a postpartum supporting apparatus according to the present invention provides reference data that is used to compare with a measurement data representing an index of body condition after childbirth for determining whether the progress of restoration of the body condition after childbirth is good or not, and result of comparison of such measurement data and reference data, so that the restoration of the body condition after childbirth can easily be evaluated. Because the reference data is provided for each of the factors that can affect the restoration of the body condition and is selected according to user specific factor, the most suitable reference data can be provided for the user.

What is claimed is:

1. A postpartum supporting apparatus, comprising:
    a storage unit; and
    an output unit, whereby,
    said storage unit stores reference data that is used to compare with postpartum measurement data representing an index of body condition after childbirth for determining whether the progress of restoration of the body condition after childbirth is good or not, said reference data being grouped with respect to factors affecting the restoration of the body condition after childbirth, and stored for each group; and
    said output unit outputs said reference data in order to compare with the postpartum measurement data representing the index of body condition after childbirth.

2. A postpartum supporting apparatus according to claim 1 in which the apparatus further comprises a measurement data input unit for inputting the postpartum measurement data representing the index of body condition after childbirth;
    a factor data input unit for inputting factor data for a user; and
    a selection unit for selecting any one of the reference data on the basis of the inputted factor data,
    said output unit further outputting the inputted postpartum measurement data and the selected reference data.

3. A postpartum supporting apparatus according to claim 2 wherein the measurement data input unit is at least either one of a measurement unit for measuring the index of the body condition or a user input unit for inputting by a user; and the factor data input unit is at least either one of a measurement unit for measuring the factor data or a user input unit for inputting by a user.

4. A postpartum supporting apparatus according to claim 1 wherein said output unit provides a graphic representation simultaneously showing on the same time-axis of postpartum time the postpartum measurement data representing the index of body condition after childbirth, and the reference data selected from the grouped reference data responsive to which factor the specific individual condition.

5. A postpartum supporting apparatus according to claim 2 wherein said output unit provides a graphic representation simultaneously showing on the same time-axis of postpartum time the postpartum measurement data representing the index of body condition after childbirth, and the reference data selected from the grouped reference data responsive to which factor meets the specific individual condition.

6. A postpartum supporting apparatus according to claim 3 wherein said output unit provides a graphic representation simultaneously showing on the same time-axis of postpartum time the postpartum measurement data representing the index of body condition after childbirth, and the reference data selected from the grouped reference data responsive to which factor meets the specific individual condition.

7. A postpartum supporting apparatus according to any one of claims 1, 2, 3, 4, 5, 6, wherein said reference data includes an ideal reference body weight increase.

8. A postpartum supporting apparatus according to claim 7 wherein said body condition is given by body weight condition.

9. A postpartum supporting apparatus according to claim 8 wherein said factors affecting the restoration of the body condition after childbirth include at least one of body weight increase during the period of pregnancy, manner of lactation and age.

10. A postpartum supporting apparatus according to claim 9 wherein the body weight condition selected as the index of body condition is given by the weight, or the body weight increase relative to the body weight, prior to pregnancy.

11. A postpartum supporting apparatus according to the claim 8 wherein the factor affecting the restoration of the body condition after childbirth is a composite factor of the body weight increase during the period of pregnancy and the manner of lactation.

12. A postpartum supporting apparatus according to claim 11 wherein the body weight condition selected as the index of body condition is given by the body weight or body weight increase relative to the body weight prior to pregnancy.

13. A postpartum supporting apparatus according to claim 1 or 6 wherein the reference data includes an ideal reference body fat rate.

14. A postpartum supporting apparatus according to claim 13 wherein the body condition is given by the body fat rate.

15. A postpartum supporting apparatus according to claim 14 wherein said factors affecting the restoration of the body condition after childbirth include at least one of the body fat rate measured one month after childbirth, the manner of lactation and the age.

16. A postpartum supporting apparatus according to claim 15 wherein the index of body condition is given by the body fat rate when the body fat is selected as the index of body condition.

17. A postpartum supporting apparatus according to claim 14 wherein the body fat factor affecting the restoration of the body condition after childbirth is a composite factor of the body fat rate measured one month after childbirth and the manner of lactation.

18. A postpartum supporting apparatus according to claim 17 wherein the body fat index of body condition is given by the body fat rate.

19. A postpartum supporting apparatus, comprising:
    a measurement data input unit;
    a storage unit;
    a comparator unit; and
    an output unit, whereby,
    said measurement data input unit inputs postpartum measurement data representing an index of body condition after childbirth;
    said storage unit stores reference data that is used to compare with the measurement data for determining whether the progress of restoration of the body condition after childbirth is good or not, said reference data being grouped with respect to factors affecting the restoration of the body condition after childbirth, and stored for each group;

said comparator unit compares the measurement data with the reference data; and said output unit outputs the result of said comparison.

20. A postpartum supporting apparatus according to claim 19 wherein the apparatus further comprises:

a factor data input unit for inputting factors selected by a user; and a selection unit for selecting any one of the reference data on the basis of the inputted factor data, wherein said comparator unit compares the measurement data with the selected reference data.

21. A postpartum supporting apparatus according to claim 20 wherein the measurement data input unit is at least one of a measurement unit for measuring the index of the body condition or a user input unit for inputting by a user; and the factor data input unit is at least one of a measurement unit for measuring the factor data or a user input unit for inputting by a user.

22. A postpartum supporting apparatus accordance to claim 19 wherein the storage unit stores pieces of advisory information useful for the restoration of the body condition after childbirth in according with the result of the comparison;

the comparison unit is responsive to the result of the comparison for selecting an appropriate piece of advisory information; and the output unit outputs at least the appropriate piece of advisory information thus selected.

23. A postpartum supporting apparatus according to claim 20 wherein the storage unit stores pieces of advisory information useful for the restoration of the body condition after childbirth in accordance with the result of the comparison;

the comparator unit is responsive to the result of the comparison for selecting an appropriate piece of advisory information; and the output unit outputs at least the appropriate piece of advisory information thus selected.

24. A postpartum supporting apparatus according to claim 21 wherein the storage unit stores pieces of advisory information useful for the restoration of the body condition after childbirth in accordance with the result of the comparison;

the comparator unit is responsive to the result of the comparison for selecting an appropriate piece of advisory information; and the output unit outputs at least the appropriate piece of advisory information thus selected.

25. A postpartum supporting apparatus according to any one of claim 19 or 20–24 wherein said reference data includes an ideal reference body weight increase.

26. A postpartum supporting apparatus according to claim 25 wherein said body condition is given by body weight condition.

27. A postpartum supporting apparatus according to claim 26 wherein said factors affecting the restoration of the body condition after childbirth include at least one of body weight increase during the period of pregnancy, manner of lactation and age.

28. A postpartum supporting apparatus according to claim 27 wherein the body weight condition selected as the index of body condition is given by the body weight or the body weight increase relative to the body weight prior to pregnancy.

29. A postpartum supporting apparatus according to claim 26 wherein the factor affecting the restoration of the body condition after childbirth is a composite factor of the body weight increase during the period of pregnancy and the manner of lactation.

30. A postpartum supporting apparatus according to claim 29 wherein the body weight condition selected as the index of the body condition is given by the body weight or body weight increase relative to the body weight prior to pregnancy.

31. A postpartum supporting apparatus according to any one of claims 19 or 20–24 wherein the reference data includes upper and lower limits for reference body weight increase.

32. A postpartum supporting apparatus according to claim 31 wherein the body condition is given by the body weight condition.

33. A postpartum supporting apparatus according to claim 32 wherein said factors affecting the restoration of the body condition after childbirth include at least one of the body weight increase during pregnancy, the manner of lactation and the age.

34. A postpartum supporting apparatus according to claim 33 wherein the body weight condition selected as the index of body condition is given by the body weight or body weight increase relative to the body weight prior to pregnancy.

35. A postpartum supporting apparatus according to claim 32 wherein said factor affecting the restoration of the body condition after childbirth is a composite factor of the body weight increase during the period of pregnancy and the manner of lactation.

36. A postpartum supporting apparatus according to claim 35 wherein the body weight condition selected as the index of body condition is given by the body weight or the body weight increase relative to the body weight prior to pregnancy.

37. A postpartum supporting apparatus according to any one of claims 19 and 20–24 wherein the reference data includes the ideal reference body fat rate.

38. A postpartum supporting apparatus according to claim 37 wherein the body condition is given by the body fat.

39. A postpartum supporting apparatus according to claim 38 wherein said factors affecting the restoration of the body condition after childbirth include at least one of the body fat rate measured one month after childbirth, the manner of lactation and the age.

40. A postpartum supporting apparatus according to claim 39 wherein the index of body condition is given by the body fat rate in case of the body fat being selected as the index of body condition.

41. A postpartum supporting apparatus according to claim 38 wherein the body fat factor affecting the restoration of the body condition after childbirth is a composite factor of the body fat rate measured one month after childbirth and the manner of lactation.

42. A postpartum supporting apparatus according to claim 41 wherein the index of body fat condition is given by the body fat rate.

43. A postpartum supporting apparatus according to any one of claims 19 or 20–24 wherein the reference data includes upper and lower limits for the reference body fat rate.

44. A postpartum supporting apparatus according to claim 42 wherein the body condition is given by the body fat.

45. A postpartum supporting apparatus according to claim 44 wherein said factors affecting the restoration of the body condition after childbirth include at least one of the body fat rate measured one month after childbirth, the manner of lactation and the age.

46. A postpartum supporting apparatus according to claim 45 wherein the index of body condition is given by the body fat rate when the body fat is selected as the index of body condition.

47. A postpartum supporting apparatus according to claim 44 wherein the body fat factor affecting the restoration of the body condition after childbirth is a composite factor of the body fat rate measured one month after childbirth and the manner of lactation.

48. A postpartum supporting apparatus according to claim 47 wherein the index of body condition is given by the body fat rate when the body fat is selected as the index of body condition.

49. A postpartum supporting apparatus according to claims 19 or 20–24 wherein the result of comparison is given by the difference between the postpartum measurement data and the reference data.

50. A postpartum supporting apparatus according to claim 49 wherein said reference data includes an ideal reference body weight increase.

51. A postpartum supporting apparatus according to claim 50 wherein said body condition is given by body weight condition.

52. A postpartum supporting apparatus according to claim 51 wherein said factors affecting the restoration of the body condition after childbirth include at least one of the body weight increase during the period of pregnancy, the manner of lactation and the age.

53. A postpartum supporting apparatus according to claim 52 wherein the body weight condition selected as the index of body condition is given by the body weight or the body weight increase relative to the body weight prior to pregnancy.

54. A postpartum supporting apparatus according to claim 51 wherein the factor affecting the restoration of the body condition after childbirth is a composite factor of the body weight increase during the period of pregnancy and the manner of lactation.

55. A postpartum supporting apparatus according to claim 54 wherein the body weight condition selected as the index of body condition is given by the body weight or the body weight increase relative to the body weight prior to pregnancy.

56. A postpartum supporting apparatus according to claim 49 wherein the reference data includes an ideal reference body fat rate.

57. A postpartum supporting apparatus according to claim 56 wherein the body condition is given by the body fat rate.

58. A postpartum supporting apparatus according to claim 57 wherein said factors affecting the restoration of the body condition after childbirth include at least one of the body fat rate measured one month after childbirth, the manner of lactation and the age.

59. A postpartum supporting apparatus according to claim 58 wherein the index of body condition is given by the body fat rate in case of the body fat being selected as the index of body condition.

60. A postpartum supporting apparatus according to claim 51 wherein the body fat factor affecting the restoration of the body condition after childbirth is a composite factor of the body fat rate measured one month after childbirth and the manner of lactation.

61. A postpartum supporting apparatus according to claim 60 wherein the index of body fat condition is given by the body fat rate.

* * * * *